US00PP25110P2

(12) United States Plant Patent
Kako

(10) Patent No.: US PP25,110 P2
(45) Date of Patent: Nov. 25, 2014

(54) *CATHARANTHUS* PLANT NAMED 'SUNNICHI TAREPA'

(50) Latin Name: *Catharanthus roseus*
Varietal Denomination: Sunnichi Tarepa

(71) Applicant: Tetsuya Kako, Shimane (JP)

(72) Inventor: Tetsuya Kako, Shimane (JP)

(73) Assignee: Suntory Flowers Ltd., Tokyo (JP)

( * ) Notice: Subject to any disclaimer, the term of this patent is extended or adjusted under 35 U.S.C. 154(b) by 86 days.

(21) Appl. No.: 13/815,120

(22) Filed: Jan. 31, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — C. A. Whealy

(57) ABSTRACT

A new and distinct cultivar of *Catharanthus* plant named 'Sunnichi Tarepa', characterized by its upright plant habit; vigorous growth habit; freely basal branching habit; freely flowering habit; long flowering period; relatively large red purple-colored flowers; and good garden performance.

1 Drawing Sheet

Botanical designation: *Catharanthus roseus.*
Cultivar denomination: 'SUNNICHI TAREPA'.

BACKGROUND OF THE INVENTION

The present invention relates to a new and distinct *Catharanthus* plant, botanically known as *Catharanthus roseus* and hereinafter referred to by the name 'Sunnichi Tarepa'.

The new *Catharanthus* plant is a product of a planned breeding program conducted by the Inventor in Higashiomi, Shiga, Japan. The objective of the breeding program is to develop new freely branching and vigorous *Catharanthus* plants with upright plant habit and numerous attractive flowers.

The new *Catharanthus* plant originated from a cross-pollination conducted by the Inventor in Higashiomi, Shiga, Japan in June, 2006 of a proprietary selection of *Catharanthus roseus* identified as code number Casp5-1, not patented, as the female, or seed, parent with a proprietary selection of *Catharanthus roseus* identified as code number Cacv10-1, not patented, as the male, or pollen, parent. The new *Catharanthus* plant was discovered and selected by the Inventor as a single flowering plant from within the progeny of the stated cross-pollination in a controlled greenhouse environment in Higashiomi, Shiga, Japan in April, 2007.

Asexual reproduction of the new *Catharanthus* plant by vegetative cuttings in a controlled greenhouse environment in Higashiomi, Shiga, Japan since April, 2007, has shown that the unique features of this new *Catharanthus* plant are stable and reproduced true to type in successive generations.

SUMMARY OF THE INVENTION

Plants of the new *Catharanthus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Sunnichi Tarepa'. These characteristics in combination distinguish 'Sunnichi Tarepa' as a new and distinct *Catharanthus* plant:

1. Upright plant habit.
2. Vigorous growth habit.
3. Freely basal branching habit.
4. Freely flowering habit.
5. Long flowering period.
6. Relatively large red purple-colored flowers.
7. Good garden performance.

Plants of the new *Catharanthus* can be compared to plants of the female parent selection. Plants of the new *Catharanthus* differ primarily from plants of the female parent selection in the following characteristics:

1. Plants of the new *Catharanthus* have larger flowers than plants of the female parent selection.
2. Plants of the new *Catharanthus* and the female parent selection differ in flower color as plants of the female parent selection have pink-colored flowers.

Plants of the new *Catharanthus* can be compared to plants of the male parent selection. Plants of the new *Catharanthus* differ primarily from plants of the male parent selection in the following characteristics:

1. Plants of the new *Catharanthus* are more upright than and not as trailing as plants of the male parent selection.
2. Plants of the new *Catharanthus* and the male parent selection differ in flower color as plants of the male parent selection have rose pink-colored flowers.

Plants of the new *Catharanthus* can be compared to plants of the *Catharanthus roseus* 'Sunnichiroin', disclosed in U.S. Plant Pat. No. 22,594. In side-by-side comparisons conducted in Higashiomi, Shiga, Japan, plants of the new *Catharanthus* differed from plants of 'Sunnichiroin' in the following characteristics:

1. Plants of the new *Catharanthus* were more upright than and not as trailing as plants of 'Sunnichiroin'.
2. Plants of the new *Catharanthus* were taller than plants of 'Sunnichiroin'.
3. Plants of the new *Catharanthus* had slightly smaller flowers than plants of 'Sunnichiroin'.
4. Plants of the new *Catharanthus* and 'Sunnichiroin' differed slightly in flower color.

BRIEF DESCRIPTION OF THE PHOTOGRAPHS

The accompanying colored photographs illustrate the overall appearance of the new *Catharanthus* plant showing the colors as true as it is reasonably possible to obtain in colored reproductions of this type. Colors in the photographs may differ slightly from the color values cited in the detailed botanical description which accurately describe the colors of the new *Catharanthus* plant.

The photograph at the top of the sheet comprises a side perspective view of a typical flowering plant of 'Sunnichi Tarepa' grown in a container.

The photograph at the bottom of the sheet comprises a close-up view of a typical flower of 'Sunnichi Tarepa'.

DETAILED BOTANICAL DESCRIPTION

The aforementioned photographs and following observations, measurements and values describe plants grown during the autumn and early winter in 15-cm containers in a polyethylene-covered greenhouse in Higashiomi, Shiga, Japan and under cultural practices typical of commercial production. During the production of the plants, day temperatures averaged 25° C. and night temperatures averaged 15° C. Plants were three months old when the description and photographs were taken. In the following description, color references are made to The Royal Horticultural Society Colour Chart, 2007 Edition, except where general terms of ordinary dictionary significance are used.

Botanical classification: *Catharanthus roseus* 'Sunnichi Tarepa'.

Parentage:

*Female, or seed, parent*.—Proprietary selection of *Catharanthus roseus* identified as code number Casp5-1, not patented.

*Male, or pollen, parent*.—Proprietary selection of *Catharanthus roseus* identified as code number Cacv10-1, not patented.

Propagation:

*Type*.—By vegetative cuttings.

*Time to initiate roots, summer*.—About two weeks at 30° C.

*Time to initiate roots, winter*.—About three weeks at 25° C.

*Time to produce a rooted young plant, summer*.—About five weeks at 30° C.

*Time to produce a rooted young plant, winter*.—About six weeks at 25° C.

*Root description*.—Fibrous; white in color.

*Rooting habit*.—Freely branching; medium density.

Plant description:

*Plant and growth habit*.—Upright plant habit; freely basal branching habit with numerous lateral branches developing per plant; vigorous growth habit.

*Plant height*.—About 28.3 cm.

*Plant diameter*.—About 39.4 cm.

Lateral branch description:

*Length*.—About 26 cm.

*Diameter*.—About 3.5 mm.

*Internode length*.—About 2.9 cm.

*Strength*.—Strong.

*Aspect*.—Upright to outwardly.

*Texture*.—Sparsely pubescent.

*Color*.—Close to 177B.

Foliage description:

*Arrangement*.—Opposite, simple.

*Length*.—About 7.7 cm.

*Width*.—About 3.2 cm.

*Shape*.—Narrowly elliptic.

*Apex*.—Broadly acute.

*Base*.—Obtuse, rounded.

*Margin*.—Entire.

*Texture, upper surface*.—Smooth, glabrous.

*Texture, lower surface*.—Sparsely pubescent.

*Venation pattern*.—Pinnate; reticulate.

*Color*.—Developing leaves, upper surface: Close to 144A. Developing leaves, lower surface: Close to 144B. Fully expanded leaves, upper surface: Close to 137A; venation, close to 144D. Fully expanded leaves, lower surface: Close to 138A; venation, close to 144D.

*Petiole*.—Length: About 4.3 mm. Diameter: About 1.7 mm. Texture, upper and lower surfaces: Sparsely pubescent. Color, upper and lower surfaces: Close to 144D overlain with close to 176D.

Flower description:

*Flower arrangement and habit*.—Single salverform flowers arising from upper leaf axils; freely flowering habit with usually about 21 flowers developing per plant; flowers face upright or outwardly.

*Fragrance*.—None detected.

*Flowering habit*.—Plants begin flowering about two to three weeks after planting; long flowering period, in the garden, plants flower continuously from the early summer to late autumn in Japan.

*Flower longevity*.—Individual flowers last about two to three days on the plant; flowers not persistent.

*Flower diameter*.—About 5.1 cm.

*Flower length* (*depth*).—About 3.4 cm.

*Tube length*.—About 2.7 cm.

*Tube diameter, at the base*.—About 1.2 mm.

*Flower buds*.—Length: About 3.4 cm. Diameter: About 4.8 mm. Shape: Cylindrical. Color: Close to 70B.

*Corolla*.—Arrangement: Five petals in a single whorl fused at the base into a tube. Petal length from throat: About 2.6 cm. Petal width: About 2.2 cm. Petal shape: Obovate. Petal apex: Mucronate. Petal margin: Entire; slightly undulate. Petal texture, upper and lower surfaces: Smooth, glabrous; velvety. Throat texture: Smooth, glabrous. Tube texture: Sparsely pubescent. Color: Petal, when opening, upper surface: Close to N74A; towards the throat, close to NN155D. Petal, when opening, lower surface: Close to 75D; towards the margins, close to N74A. Petal, fully opened, upper surface: Close to 74B; towards the throat, close to NN155D. Petal, fully opened, lower surface: Close to 75D; towards the margins, close to 75A. Throat: Close to 145C. Tube: Close to 154C overlain with close to 58D.

*Calyx*.—Arrangement: Star-shaped tubular calyx with five sepals fused towards the base. Sepal length: About 3.4 mm. Sepal width: About 0.7 mm. Sepal shape: Lanceolate. Sepal apex: Acute. Sepal margin: Entire. Sepal texture, upper and lower surfaces: Sparsely pubescent. Color, immature and mature, upper surface: Close to 143B. Color, immature and mature, lower surface: Close to 143B.

*Peduncles*.—Length: About 3.7 mm. Diameter: About 1.4 mm. Angle: Upright to outwardly. Strength: Strong. Texture: Smooth, glabrous. Color: Close to 144D.

*Reproductive organs*.—Stamens: Quantity per flower: Five. Stamen length: About 3.3 mm. Anther shape: Narrowly elliptic. Anther size: About 1.3 mm by 3.3 mm. Anther color: Close to 4C. Pollen amount: Moderate. Pollen color: Close to 2D. Pistils: Quantity per flower: One. Pistil length: About 2.2 cm. Style color: Close to 145C. Stigma shape: Transversely ellipsoidal. Stigma color: Close to 145A. Ovary color: Close to 145A. Seeds and fruits: Seed and fruit development have not been observed on plants of the new *Catharanthus*.

Garden performance: Plants of the new *Catharanthus* have been observed to have good garden performance and to tolerate wind, rain and temperatures ranging from about 5° C. to about 35° C. to 40° C.

Pathogen & pest resistance: Plants of the new *Catharanthus* have not been observed to be resistant to pathogens and pests common to *Catharanthus* plants.

It is claimed:

1. A new and distinct *Catharanthus* plant named 'Sunnichi Tarepa' as illustrated and described.

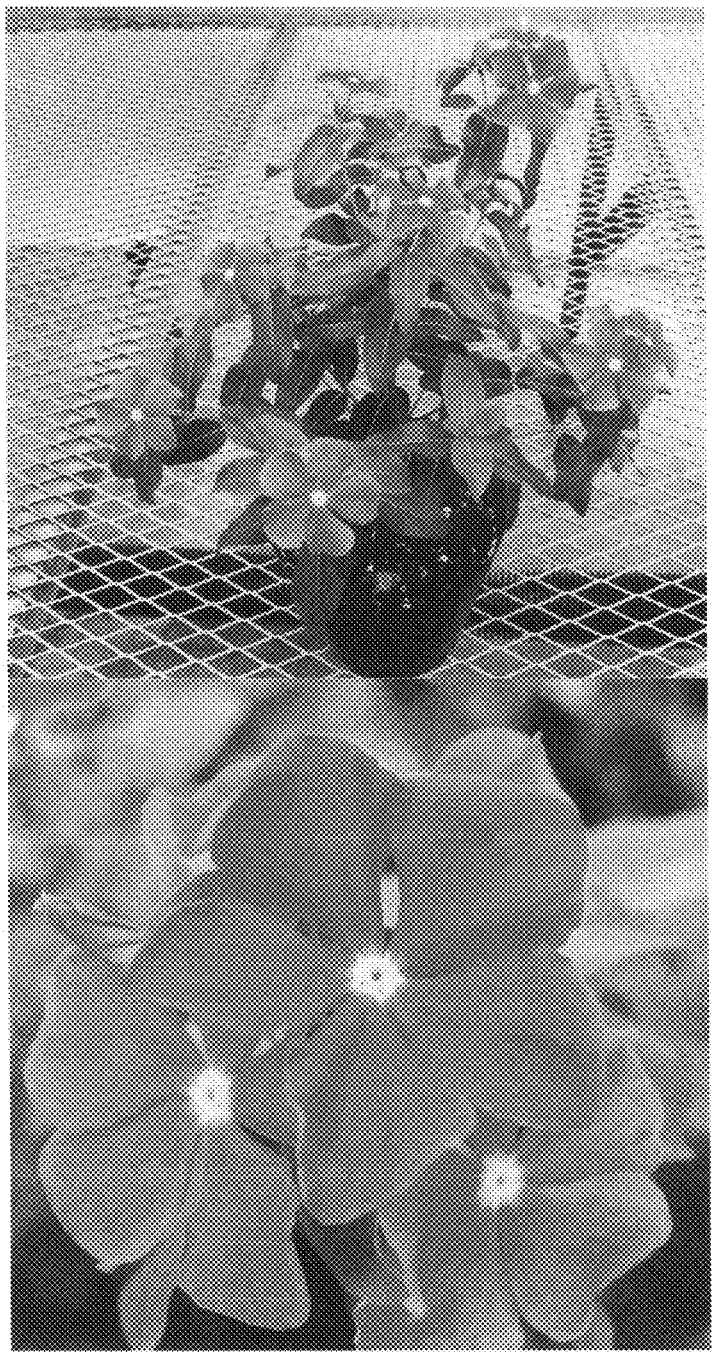

* * * * *